United States Patent
Kim et al.

(10) Patent No.: US 9,737,220 B2
(45) Date of Patent: Aug. 22, 2017

(54) APPARATUS AND METHOD FOR MEASURING BIOSIGNAL

(71) Applicant: SAMSUNG ELECTRONICS CO., LTD., Suwon-si (KR)

(72) Inventors: JongPal Kim, Seoul (KR); Byunghoon Ko, Hwaseong-si (KR); Sangyun Park, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 13 days.

(21) Appl. No.: 14/968,975

(22) Filed: Dec. 15, 2015

(65) Prior Publication Data

US 2017/0007138 A1    Jan. 12, 2017

(30) Foreign Application Priority Data

Jul. 7, 2015   (KR) ......................... 10-2015-0096547

(51) Int. Cl.
*A61B 5/024* (2006.01)
*A61B 5/00* (2006.01)
*A61B 5/1455* (2006.01)
*A61B 5/02* (2006.01)
*A61B 5/021* (2006.01)
*A61B 5/026* (2006.01)

(52) U.S. Cl.
CPC .......... *A61B 5/02427* (2013.01); *A61B 5/021* (2013.01); *A61B 5/02007* (2013.01); *A61B 5/02416* (2013.01); *A61B 5/02438* (2013.01); *A61B 5/14552* (2013.01); *A61B 5/6826* (2013.01); *A61B 5/7207* (2013.01); *A61B 5/0261* (2013.01); *A61B 5/1455* (2013.01)

(58) Field of Classification Search
None
See application file for complete search history.

(56) References Cited

U.S. PATENT DOCUMENTS

| | | | |
|---|---|---|---|
| 4,258,719 A | 3/1981 | Lewyn | |
| 5,766,131 A | 6/1998 | Kondo et al. | |
| 9,155,473 B2 * | 10/2015 | Kang | ............... A61B 5/0071 |
| 2002/0095092 A1 | 7/2002 | Kondo et al. | |

(Continued)

FOREIGN PATENT DOCUMENTS

| | | |
|---|---|---|
| JP | 2003-61957 A | 3/2003 |
| JP | 2006-43146 A | 2/2006 |

(Continued)

OTHER PUBLICATIONS

Extended European Search Report issued on Nov. 14, 2016 in counterpart European Patent Application No. 16152026.7 (10 pages, in English).

*Primary Examiner* — Brian T Gedeon
(74) *Attorney, Agent, or Firm* — NSIP Law

(57) ABSTRACT

An apparatus and a method of measuring a biosignal are provided. The apparatus of measuring a biosignal includes an optical source configured to emit a first light and a second light towards a target, an inserted layer configured to transmit the first light and to reflect the second light, and an optical detector configured to detect a first received light that corresponds to the first light reflected by or transmitted through the target, and to detect a second received light that corresponds to the second light reflected by the inserted layer.

20 Claims, 15 Drawing Sheets

(56) References Cited

U.S. PATENT DOCUMENTS

| | | |
|---|---|---|
| 2008/0221488 A1 | 9/2008 | Kurono et al. |
| 2010/0217098 A1 | 8/2010 | LeBoeuf et al. |
| 2013/0131519 A1 | 5/2013 | LeBoeuf et al. |
| 2014/0058217 A1 | 2/2014 | Giovangrandi |

FOREIGN PATENT DOCUMENTS

| | | |
|---|---|---|
| JP | 2013-106837 A | 6/2013 |
| JP | 2014-068733 A | 4/2014 |
| JP | 2014-079352 A | 5/2014 |
| JP | 2015-039542 A | 3/2015 |
| KR | 10-2004-0015311 | 2/2004 |
| KR | 10-2006-0116635 A | 11/2006 |
| KR | 10-2009-068657 A | 6/2009 |

\* cited by examiner

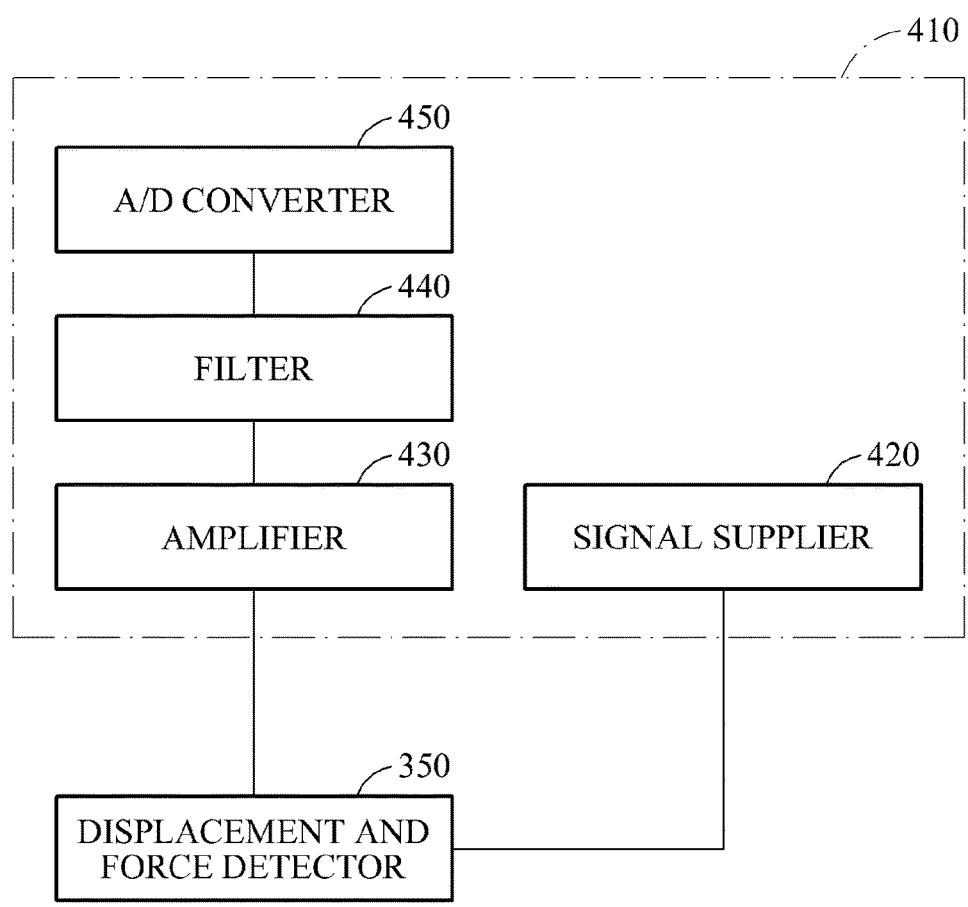

APPARATUS AND METHOD FOR MEASURING BIOSIGNAL

CROSS-REFERENCE TO RELATED APPLICATION

This application claims the benefit under 35 USC 119(a) of Korean Patent Application No. 10-2015-0096547, filed on Jul. 7, 2015, in the Korean Intellectual Property Office, the entire disclosure of which is incorporated herein by reference for all purposes.

BACKGROUND

1. Field

The following description relates to an apparatus and a method for measuring a biosignal.

2. Description of Related Art

Due to the widespread use of personal electronic devices such as smartphones, tablets and laptops, researches have been conducted to apply the measurement of a biosignal of an individual to various fields such as in health-care, wellness and exercise, entertainment, human-machine interface and the like. A heartbeat is an example of a biosignal that may provide various information about a person, such as a stress state or an exercise state of the person. Further, the measurement of a heartbeat is relatively convenient. Thus, the measurement of a heart beat may be applied in many application fields. To measure a heartbeat, a photoplethysmogram (PPG) or an electrocardiogram (ECG) based method is widely used. Unlike an ECG that is generally measured by placing a plurality probe on a torso of a person, a PPG may be readily measured from end portions of a body such as, for example, a wrist and a fingertip. The method of measuring a heartbeat using a PPG may involve emitting light beneath skin, measuring light reflected from a body tissue or light transmitted through the body tissue, and restoring a pulse wave of blood passing through the body tissue.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an apparatus for measuring a biosignal including an optical source configured to emit a first light and a second light towards a target, an inserted layer configured to transmit the first light and to reflect the second light, and an optical detector configured to detect a first received light that corresponds to the first light reflected by or transmitted through the target, and to detect a second received light that corresponds to the second light reflected by the inserted layer.

A wavelength of the first light may be longer than a wavelength of the second light.

The first light may be a light polarized at a first angle. The second light may be a light polarized at a second angle different from the first angle. The inserted layer may be configured to transmit the light polarized at the first angle and reflect the light polarized at the second angle.

The first received light may have an optical property that varies based on a change in blood flow in the target.

The second received light may have an optical property that varies based on a change in surface displacement of the target or a change in contact force on a surface of the target.

The inserted layer may be physically deformable by an external force.

The inserted layer may be a sticker or a tattoo attached to a surface of the target.

The general aspect of the apparatus may further include a signal processor configured to extract biosignal information based on at least one signal input from the optical detector.

The general aspect of the apparatus for measuring a biosignal may operate through being comprised in a mobile device or a wearable device.

The general aspect of the apparatus may further include a shield configured to prevent an inflow of an external light into the optical detector.

The optical source may include a first optical source disposed on one side of the shield and configured to emit the first light towards the target, and a second optical source disposed on another side of the shield and configured to emit the second light towards the target.

The optical detector may include a first optical detector disposed on one side of the shield and configured to detect the first light transmitted through the target, and a second optical detector disposed on another side of the shield and configured to detect the second light reflected by the inserted layer.

In another general aspect, an apparatus for measuring a biosignal includes an optical source configured to emit a light towards a target, an inserted layer configured to transmit the light, an optical detector configured to detect a light reflected by the target or a light transmitted through the target, and a displacement and force detector configured to detect either a change in displacement on a surface of the target or a change in contact force on the surface of the target.

The displacement and force detector may be disposed in a single layer structure or a multilayer structure in the inserted layer.

The displacement and force detector may be configured to detect either the change in displacement or the change in contact force by using a piezoelectric element or a piezoresistive element.

The displacement and force detector may include a first electrode formed on the inserted layer, and a second electrode located to be spaced apart from the first electrode.

The displacement and force detector may be configured to detect at least one of the change in displacement and the change in contact force based on a change in capacitance based on a change in distance between the first electrode and the second electrode.

The general aspect of the apparatus may further include a signal processor configured to obtain biosignal information of the target based on either a signal to be input from the optical detector or a signal to be input from the displacement and force detector.

In another general aspect, a method of a biosignal measuring apparatus to measure a biosignal involves emitting a first light towards a target, detecting a first received light corresponding to the first light either reflected by the target or transmitted through the target, emitting a second light towards the target, detecting a second received light corresponding to the second light that is reflected by the inserted layer, and obtaining biosignal information of the target based on at least one of the detected first light and the detected second light.

In yet another general aspect, an apparatus for measuring a biosignal, includes an optical source configured to emit a first emitted light of a first wavelength and a second emitted light of a second wavelength, an inserted layer configured to separate the first emitted light and the second emitted light, and an optical detector configured to detect a first received light corresponding the first emitted light that is reflected or transmitted by a target and a second received light corresponding to the second emitted light that is separated from the first emitted light by the inserted layer.

The insertion layer may be configured to separate the first emitted light and the second emitted light based on a wavelength of a light incident on the insertion layer.

The general aspect of the apparatus may further including a signal processor configured to extract biosignal information based on a signal obtained from the optical detector, and the biosignal information may include at least one of a heartbeat, a blood oxygen saturation level, a blood pressure, and a blood vessel elasticity.

Other features and aspects will be apparent from the following detailed description, the drawings, and the claims.

BRIEF DESCRIPTION OF THE DRAWINGS

FIG. 4 is a diagram illustrating an operation of an example of a second signal measurer.

Figure 1:
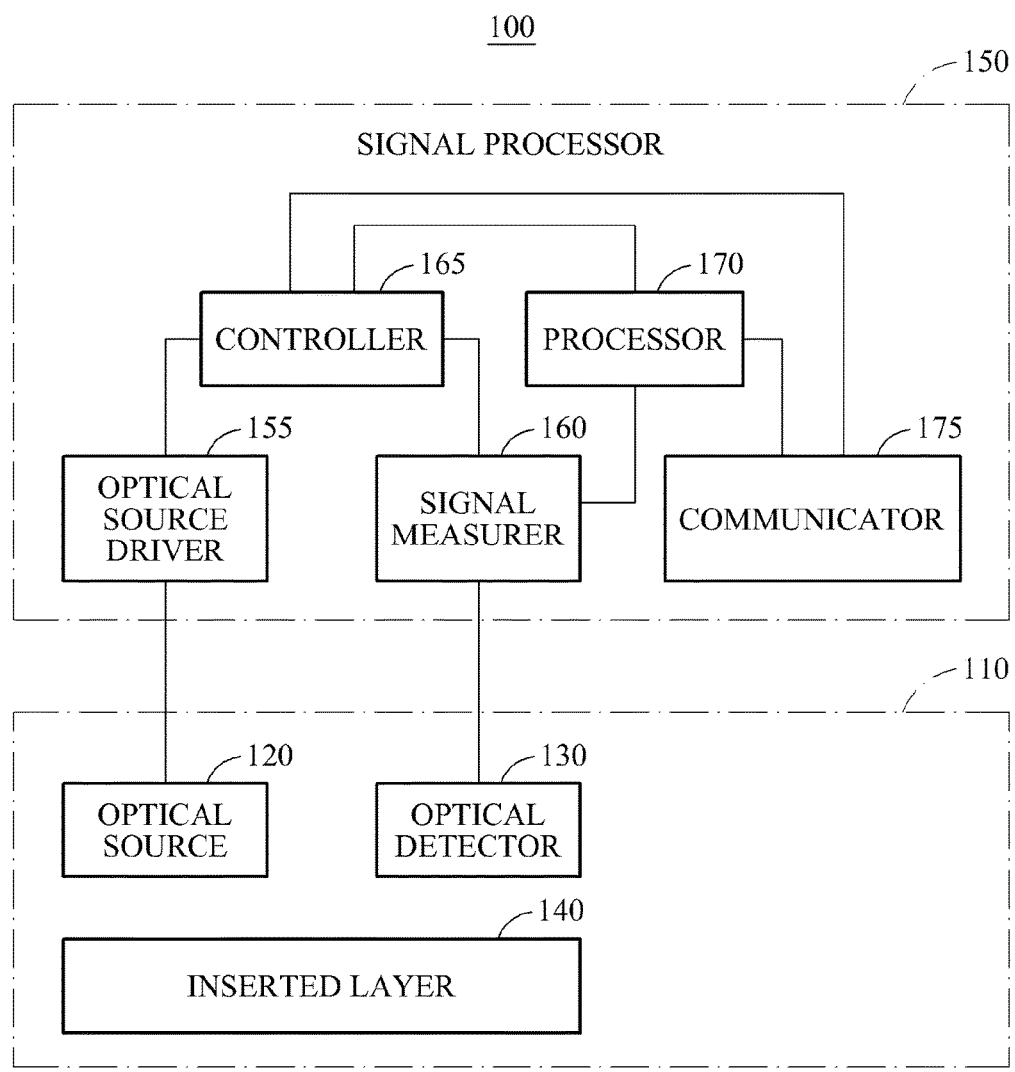
FIG. 1 is a diagram illustrating an operation of an example of an apparatus for measuring a biosignal.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

FIG. 1 is a diagram illustrating an operation of an example of an apparatus for measuring a biosignal. Hereinafter, the apparatus for measuring a biosignal will be referred to as a biosignal measuring apparatus. In the example of FIG. 1, the biosignal measuring apparatus 100 measures a biosignal of a target on whom the measurement is performed. For example, the biosignal measuring apparatus 100 may measure a photoplethysmogram (PPG) signal from a portion for measurement take from a wrist, an ear, a finger, a toe of a user and the like, and may extract information associated with a heartbeat, a blood oxygen saturation ($SpO_2$), a blood pressure, a blood vessel elasticity and the like, from the measured PPG. For another example, the biosignal measuring apparatus 100 may measure a change in displacement or a change in contact force on a surface of the portion for measurement, and may extract biosignal information based on the measured change in displacement or in contact force. The biosignal measuring apparatus 100 may operate through being included in a mobile device or a wearable device that is worn on the user, in addition to a diagnostic device.

Referring to FIG. 1, the biosignal measuring apparatus 100 includes a biosignal measuring sensor 110 and a signal processor 150. The biosignal measuring sensor 110 includes an optical source 120, an optical detector 130, and an inserted layer 140. The signal processor 150 includes an optical source driver 155, a signal measurer 160, a controller 165, a processor 170, and a communicator 175.

The biosignal measuring sensor 110 is attached to the target and measures a biosignal of the target. For example, the biosignal measuring sensor 110 may measure a light reflected in a blood vessel of the target or a light transmitted through the blood vessel, and measure a change in vascular volume depending on a dilatation or a contraction of the blood vessel of the target.

The optical source driver 155 outputs a driving signal to drive the optical source 120. The optical source 120 selectively emits different types of light having different wavelengths towards the target based on the driving signal received from the optical source driver 155. For example, the optical source 120 may include an optical source configured to emit a light having a long wavelength, and an optical source configured to emit a light having a short wavelength. For example, a light-emitting diode (LED) and a laser diode may be used as the optical sources. The controller 165 controls the optical source driver 155 to control a type of light to be emitted from the optical source 120 and a time section during which the light is emitted.

The inserted layer 140 selectively transmits or reflects the light emitted from the optical source 120. For example, the inserted layer 140 may transmit the long-wavelength light emitted from the optical source 120, and reflect the short-wavelength light emitted from the optical source 120. By using an inserted layer 140 having such selectivity, the biosignal measuring sensor 110 may identify each of a deep reflected wave and a surface reflected wave and separately measure each wave. The inserted layer 140 may be provided in a form of a flexible thin film such that the inserted layer 140 may be deformed by an external force. For example, the inserted layer 140 may include an elastic material such as a silicon-based material, and be provided in a layered form including at least one layer.

The biosignal measuring sensor 110 may be classified into a reflective structure and a transmissive structure based on a biosignal measuring type. A biosignal measuring sensor in the reflective structure may measure an amount of light to be reflected by the target after light is emitted towards the target. A biosignal measuring sensor in the transmissive structure may measure an amount of light to be transmitted, without being absorbed, through the target after light is emitted towards the target.

According to an example of a biosignal measuring sensor 110 having a reflective structure, a light emitted from the optical source 120 and transmitted through the inserted layer 140 may be reflected from a deep portion of the target, and the light reflected from the deep portion may be detected by the optical detector 130. A deep reflected wave detected through such a process may include information associated with a change in vascular volume depending on a dilatation or a contraction of a blood vessel in the target. The light reflected by the inserted layer 140 may be detected by the optical detector 130, and a surface reflected wave detected through such a process may include information associated with a change in surface displacement or in contact force depending on the dilatation or the contraction of the blood vessel. For example, a photodiode, a charge-coupled device (CCD), and a phototransistor may be used as the optical detector 130.

According to an example of a biosignal measuring sensor 110 having a transmissive structure, a portion of light emitted from the optical source 120 and transmitted through the inserted layer 140 may transmit through the target, and the portion of the light transmitted through the target may be detected by the optical detector 130. A deep transmitted wave detected through such a process may include information associated with an amount of the transmitted light depending on a change in amount of blood in the target. For example, in response to the dilation of a blood vessel dilates and an increase in an amount of blood in the tissue, an amount of light transmitted through the target may decrease. Conversely, in response to the contraction of the blood vessel and a decrease in an amount of blood in the tissue, an amount of light transmitted through the target may increase.

Figure 2:
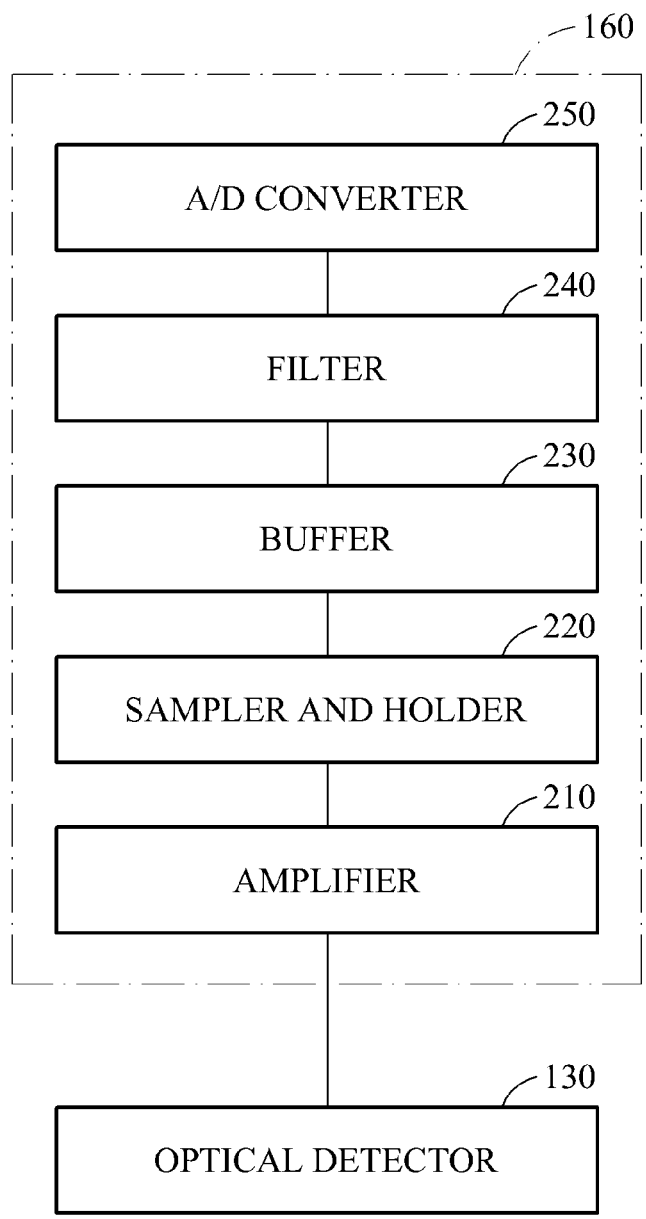
FIG. 2 is a diagram illustrating an operation of an example of a signal measurer.

A signal detected by the optical detector 130 is transferred to the signal measurer 160. The signal measurer 160 performs signal processing on the detected signal. The signal processing may involve, for example, amplifying, filtering, and converting the detected signal to a digital signal. In one example illustrated in FIG. 2, the signal measurer 160 includes an amplifier 210 configured to amplify the signal transferred from the optical detector 130, a sampler and holder 220 configured to sample and hold the amplified signal, a buffer 230 configured to receive the sampled and held signal, a filter 240 configured to filter the signal received from the buffer 230, and an analog-to-digital (A/D) converter 250 configured to convert the signal on which the filtering is performed to a digital signal. In this example, through the filtering, it is possible to eliminate a frequency component other than a desirable frequency component or to eliminate noise included in the signal.

The signal measurer 160 measures an optical signal detected in a time section during which the optical source 120 is activated and an optical signal detected in a time section during which the optical source 120 is inactivated, respectively, under control of the controller 165. For example, the controller 165 may adjust a sampling timing and a holding timing of the sampler and holder 220 to extract the optical signal detected in the time section in which the optical source 120 is activated. Referring back to FIG. 1, the processor 170 extracts the biosignal information from the signal output from the signal measurer 160. The processor 170 is controlled by the controller 165.

A signal quality of deep information such as the deep reflected wave or the deep transmitted wave and of surface information such as the surface reflected wave may vary depending on a target to be measured or an environment in which measurement is performed. The processor 170 extracts the biosignal information based on one of the deep information and the surface information which has a more desirable signal quality, or extracts the biosignal information by combining the deep information and the surface information. Based on an application, the processor 170 obtains information associated with a heartbeat, an $SpO_2$, a blood pressure, a blood vessel elasticity and the like, from the deep information and the surface information based on an application.

According to one example, the surface information from the light reflected by the inserted layer 140 may be used to estimate a motion artifact. For example, the processor 170 may estimate a motion artifact included in the deep information based on the surface information, and perform adaptive filtering on the estimated motion artifact and the deep information to eliminate the motion artifact from the deep information. The processor 170 may extract the biosignal information from the deep information from which the motion artifact is eliminated.

In this example, the communicator 175 transmits to the outside of the signal processor 150, the biosignal information extracted by the processor 170 under control of the controller 165.

Figure 3:
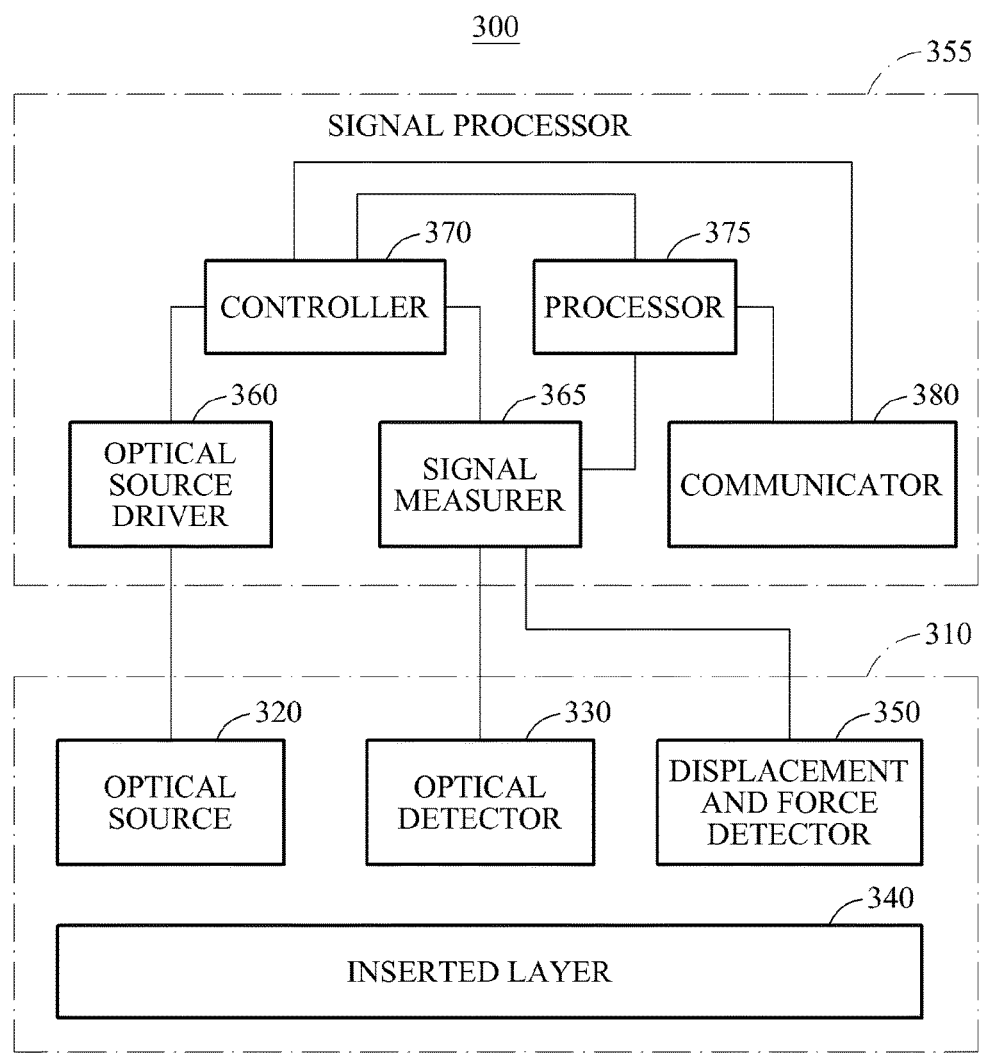
FIG. 3 is a diagram illustrating an operation of another example of an apparatus for measuring a biosignal.

FIG. 3 is a diagram illustrating another example of an operation of a biosignal measuring apparatus 300. Referring to FIG. 3, the biosignal measuring apparatus 300 includes a biosignal measuring sensor 310 and a signal processor 355. The biosignal measuring sensor 310 includes an optical source 320, an optical detector 330, an inserted layer 340, and a displacement and force detector 350. The signal processor 355 includes an optical source driver 360, a signal measurer 365, a controller 370, a processor 375, and a communicator 380.

The biosignal measuring sensor 310 measures surface information based on a change in displacement or in contact force on a surface of a target to be measured, in addition to deep information of the target based on a change in vascular volume, using light. A dilatation and a contraction of a blood vessel in the target may apply a force to the surface of the target and generate a displacement or a contact force of the surface, and thus the biosignal measuring sensor 310 measures such a displacement or contact force of the surface. For example, the biosignal measuring sensor 310 may simultaneously measure, in a same measurement portion, pulse wave information using light and pulse wave information using a displacement or a contact force of skin.

The optical source driver 360 outputs a driving signal to drive the optical source 320 under control of the controller 370, and the optical source 320 emits at least one type of light towards the target based on the driving signal. The inserted layer 340 transmits a light emitted from the optical source 320. The optical detector 330 detects a light reflected from a deep portion of the target after emitted from the optical source 320, or a light transmitted through the target after emitted from the optical source 320.

The displacement and force detector 350 detects the change in displacement and contact force of the surface based on a change in blood flow in the target. Alternatively, the displacement and force detector 350 measures a change in pressure based on the change in displacement or contact force of the surface. In an example, the displacement and force detector 350 may be formed in a single-layer structure or a multi-layer structure in the inserted layer 340, and detect a displacement or a contact force of skin based on a vibration of a pulse wave of the target. The displacement and force detector 350 may include a piezoelectric element or a piezoresistive element configured to output, as a change in electrical signal, the change in displacement or contact force depending on the change in blood flow. The signal processor 355 obtains biosignal information by selectively using a signal obtained by the optical detector 330 and a signal obtained by the displacement and force detector 350, or by combining the two signals.

The signal obtained by the optical detector 330 and the signal obtained by the displacement and force detector 350 are transferred to the signal measurer 365. In an example, the signal measurer 365 may include a first signal measurer (not shown) configured to process the signal detected by the optical detector 330, and a second signal measurer 410 configured to process the signal detected by the displacement and force detector 350. The first signal measurer may include the amplifier 210, the sampler and holder 220, the buffer 230, the filter 340, and the A/D converter 250, which are included in the signal measurer 160 of FIG. 2.

Referring to FIG. 4, the second signal measurer 410 includes a signal supplier 420 configured to supply an electrical signal used for the displacement and force detector 350 to measure the surface displacement or the contact force, an amplifier 430 configured to amplify the signal transferred from the displacement and force detector 350, a filter 440 configured to perform filtering on the amplified signal, and an A/D converter 450 configured to convert the signal obtained through the filtering to a digital signal. Referring back to FIG. 3, the processor 375 extracts the biosignal information from the signal output from the signal measurer 365. The extracted biosignal information may be externally transmitted through the communicator 380. The controller 370 controls respective operations of the optical source driver 360, the signal measurer 365, the processor 375, and the communicator 380.

Figure 5A:
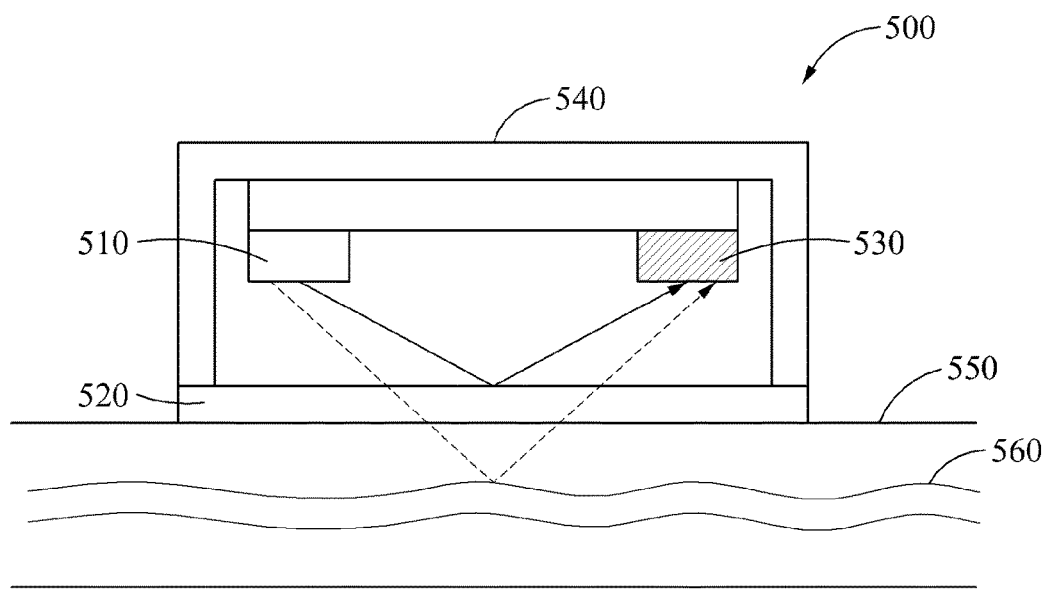
FIGS. 5A and 5B are diagrams illustrating an example of a biosignal measuring sensor in a reflective structure.
Figure 5B:
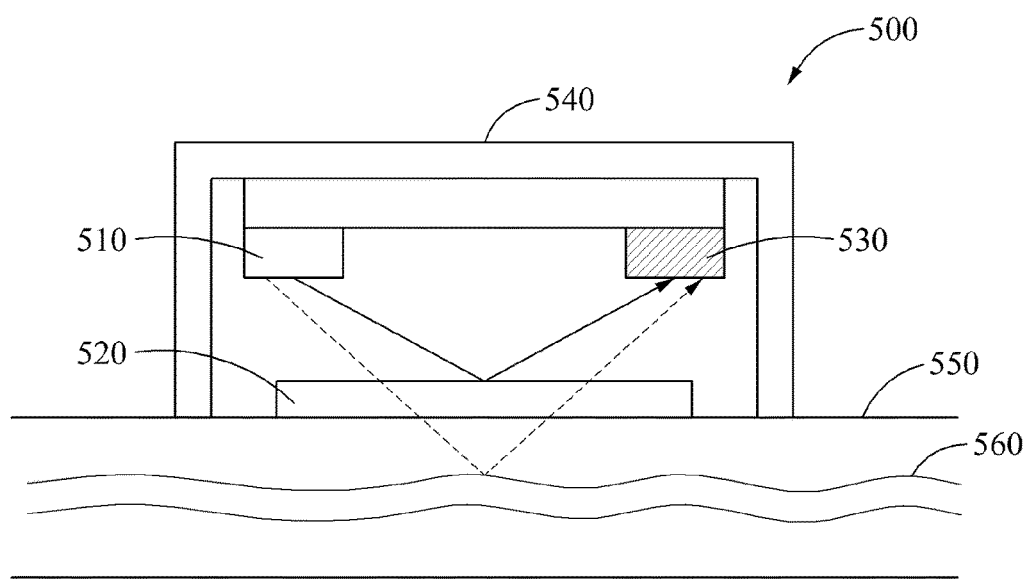

FIGS. 5A and 5B illustrate an example of a biosignal measuring sensor 500 having a reflective structure. Referring to FIGS. 5A and 5B, the biosignal measuring sensor 500 includes an optical source 510, an inserted layer 520, an optical detector 530, and a shield 540. The optical source 510 selectively emits a first light and a second light towards a target 550. For example, the first light is a light having a long wavelength, for example, infrared light and red light. The second light is a light having a short wavelength, for example, blue light.

The inserted layer 520 transmits the first light and reflects the second light. The inserted layer 520 may be combined in the biosignal measuring sensor 500 as illustrated in FIG. 5A. Alternatively, in another example illustrated in FIG. 5B, the inserted layer 520 is configured to be detachable from the biosignal measuring sensor 500, for instance, in a form of a sticker or a temporary tattoo attached to a surface of the target 550, or a skin of the user.

The optical detector 530 detects a first light reflected from a deep portion of the target 550 and a second light reflected by the inserted layer 520. For example, the first light reflected from the deep portion of the target 550 may include deep reflected wave information based on a change in vascular volume of a blood vessel 560 in the target 550. The second light reflected by the inserted layer 520 may include surface reflected wave information based on a change in vascular volume of the blood vessel 560 in the target 550. The first light reflected from the deep portion of the target 550 may have an optical property that may vary depending on a change in blood flow in the target 550. For example, an amount of light to be reflected or a wavelength of the light to be reflected may vary depending on the change in blood flow. The second light reflected by the inserted layer 520 may have an amount of light that may vary based on a surface displacement or a contact force of the target 550 depending on the change in blood flow in the target 550. The shield 540 is provided on an outer side of the optical source 510 and the optical detector 530, and blocks an inflow of an external light into the optical detector 530. The shield 540 may serve a function as a housing or a case configured to protect components or elements of the biosignal measuring sensor 500.

Alternatively, the optical source 510 selectively emits a first light polarized at a first angle and a second light polarized at a second angle. The inserted layer 520 may serve a function of a polarizing filter configured to transmit the light polarized at the first angle and reflect the light polarized at the second angle. For example, the first light may be polarized or linearly polarized at 0°, and the second light may be polarized or rotatingly polarized at 90°.

Figure 6:
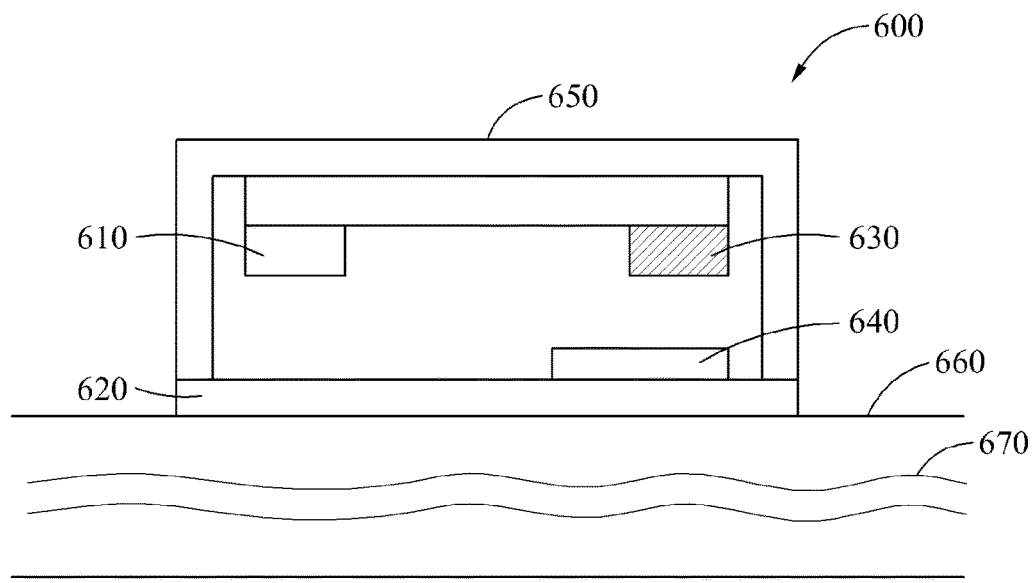
FIG. 6 is a diagram illustrating another example of a biosignal measuring sensor in a reflective structure.
Figure 7:
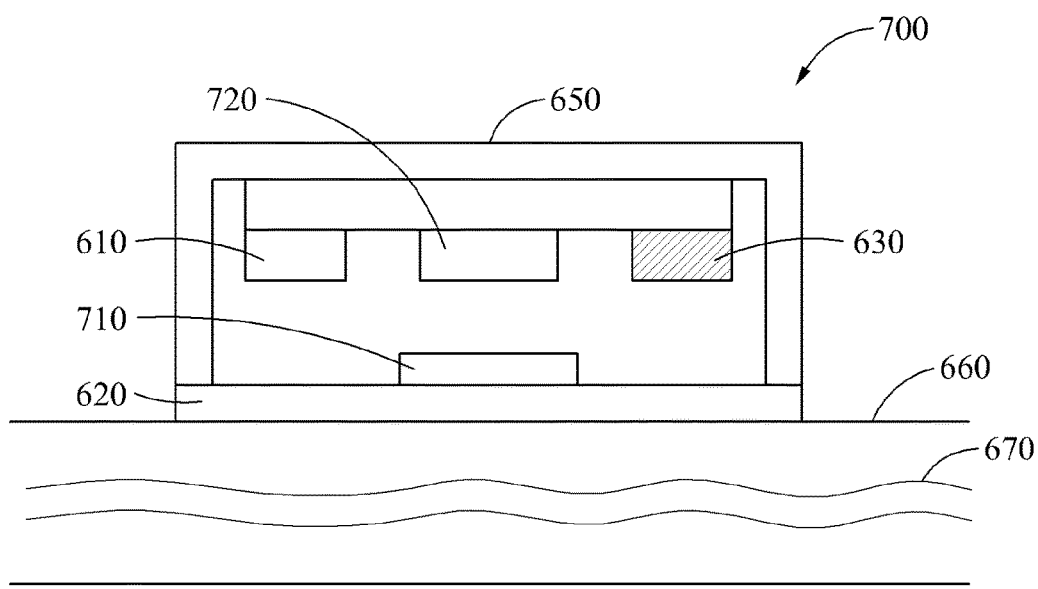
FIG. 7 is a diagram illustrating still another example of a biosignal measuring sensor in a reflective structure.

FIGS. 6 and 7 are diagrams illustrating additional examples of biosignal measuring sensors having a reflective structure. Referring to FIG. 6, a biosignal measuring sensor 600 includes an optical source 610, an inserted layer 620, an optical detector 630, a displacement and force detector 640, and a shield 650. The optical source 610 emits a long-wavelength light, for example, infrared light and red light, towards a target 660. The inserted layer 620 transmits a light emitted from the optical source 610. The optical detector 630 detects a light reflected from a deep portion of the target 660. The light reflected from the deep portion may include deep reflected wave information based on a change in vascular volume of a blood vessel 670 in the target 660. The shield 650 is provided on an outer side of the optical source 610 and the optical detector 630, and blocks an inflow of an external light into the optical detector 630.

The displacement and force detector 640 measures a surface displacement or a contact force of the target 660 from a vibration of a pulse wave. The displacement and force detector 640 may be formed in a signal-layer structure or a multi-layer structure in the inserted layer 620. A pulse wave of the target 660 may be extracted from the measured surface displacement or the contact force of the target 660. In an example illustrated in FIG. 6, the displacement and force detector 640 may detect a change in surface displacement or contact force using a piezoelectric element or a piezoresistive element configured to output, as a change in electrical signal, the surface displacement or the contact force of the target 660. The piezoresistive element may be a strain gauge. According to an example, the piezoelectric element or the piezoresistive element may be formed on the inserted layer 620.

Alternatively, a displacement and force detector may detect a change in surface displacement or contact force of the target 660 by measuring a change in capacitance. Referring to FIG. 7, a biosignal measuring sensor 700 includes a first electrode 710 and a second electrode 720 which form a capacitor. The first electrode 710 is formed on the inserted layer 620, and the second electrode 720 is located separately from the first electrode 710. For example, the first electrode 710 may be formed by doping a conductive material in the inserted layer 620 formed with a silicon-based material.

A vibration of a pulse wave may generate a vibration of a surface of the target 660, and a distance between the first electrode 710 and the second electrode 720 may change depending on the surface vibration of the target 660. A capacitance of the capacitor formed by the first electrode 710 and the second electrode 720 may be also determined based on the distance between the first electrode 710 and the second electrode 720. The displacement and force detector may detect a change in surface displacement or contact force in which a pulse wave signal is reflected based on the change in capacitance depending on the distance between the first electrode 710 and the second electrode 720.

Figure 8A:
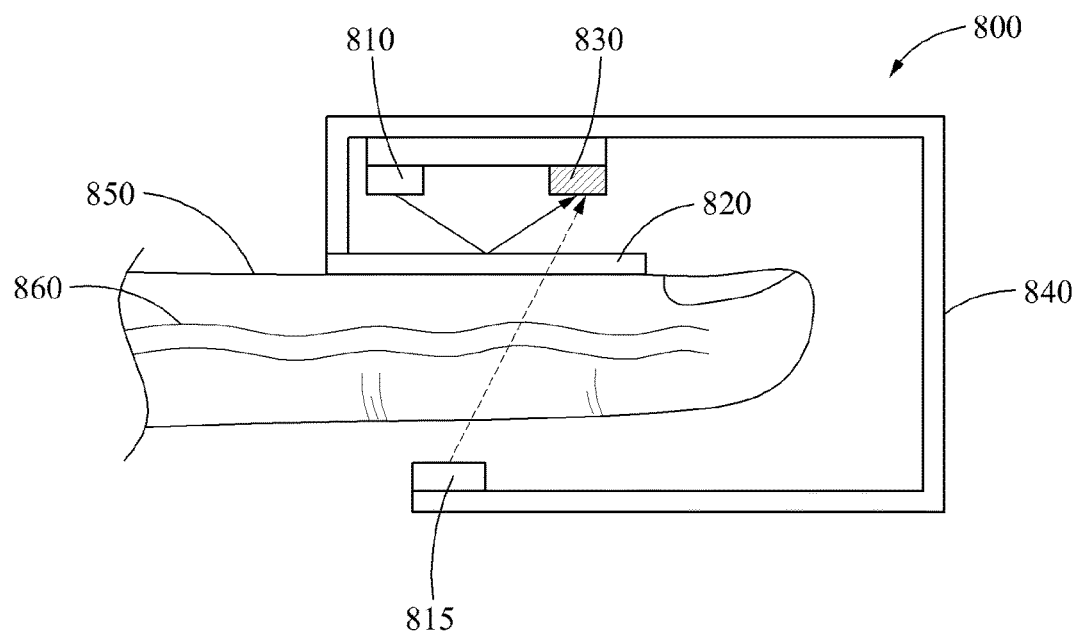
FIGS. 8A and 8B are diagrams illustrating an example of a biosignal measuring sensor having a transmissive structure.
Figure 8B:
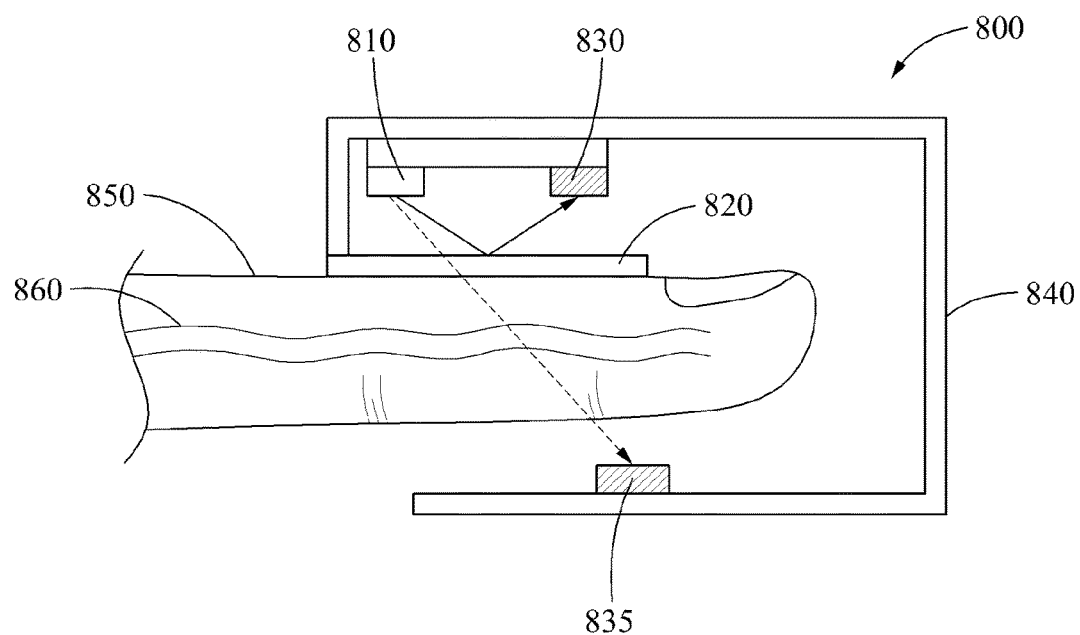

FIGS. 8A and 8B are diagrams illustrating examples of biosignal measuring sensors 800 having a transmissive structure. Referring to FIG. 8A, the biosignal measuring sensor 800 includes an optical source, an inserted layer 820, an optical detector 830, and a shield 840. The optical source includes a first optical source 815 configured to emit a first light towards a target 850 and a second optical source 810 configured to emit a second light towards the target 850. A portion of the first light emitted from the first optical source 815 may be transmitted through the target 850, and the light transmitted through the target 850 may be detected by the optical detector 830. A portion or an entirety of the second light emitted from the second optical source 810 may be reflected by the inserted layer 820, and the light reflected by the inserted layer 820 may be detected by the optical detector 830. An amount of the transmitted light to be detected by the optical detector 830 may vary depending on a change in blood flow from a dilatation or a contraction of a blood vessel 860 in the target 850. The first optical source 815 may be located on one side of the shield 840 and the second optical source 810 may be located on another side of the shield 840.

In another example, the first optical source 815 may alternatively emit a first light polarized at a first angle, and the second optical source 810 may emit a second light polarized at a second angle based on a control signal. The inserted layer 820 may transmit the light polarized at the first angle, and reflect the light polarized at the second angle.

Referring to FIG. 8B, the biosignal measuring sensor 800 includes an optical source 810 configured to selectively emit a first light and a second light, and a first optical detector 835 configured to detect a first light transmitted through the target 850 and a second optical detector 830 configured to detect a second light reflected by the inserted layer 820. The first optical detector 835 may be located on one side of the shield 840, and the optical source 810 and the second optical detector 830 may be located on another side of the shield 840.

Figure 9:
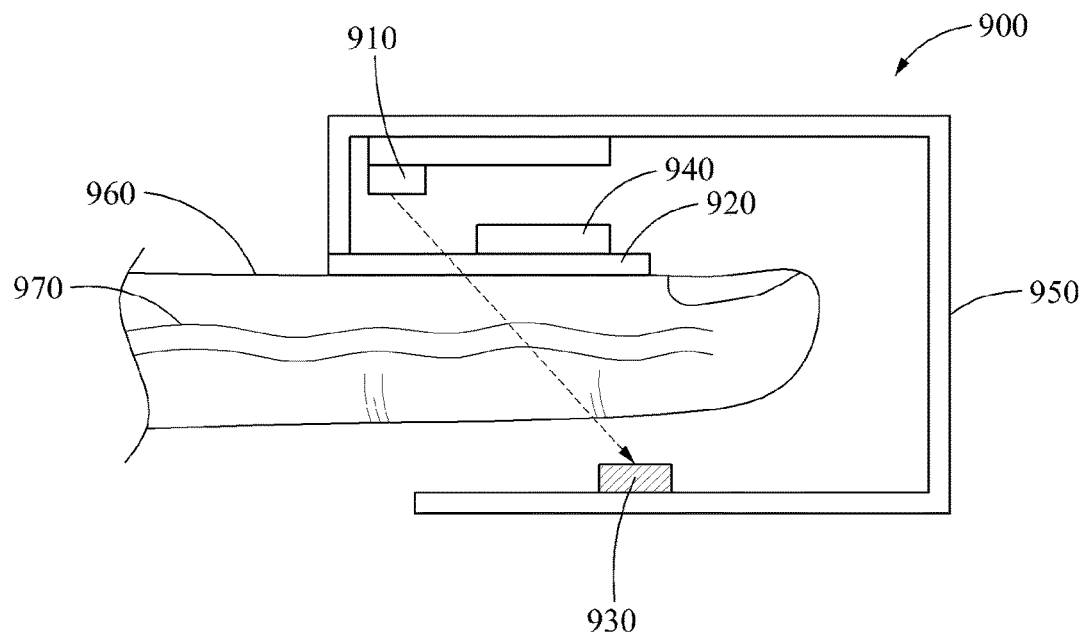
FIGS. 9 and 10 are diagrams illustrating another example of a biosignal measuring sensor having a transmissive structure.
Figure 10:
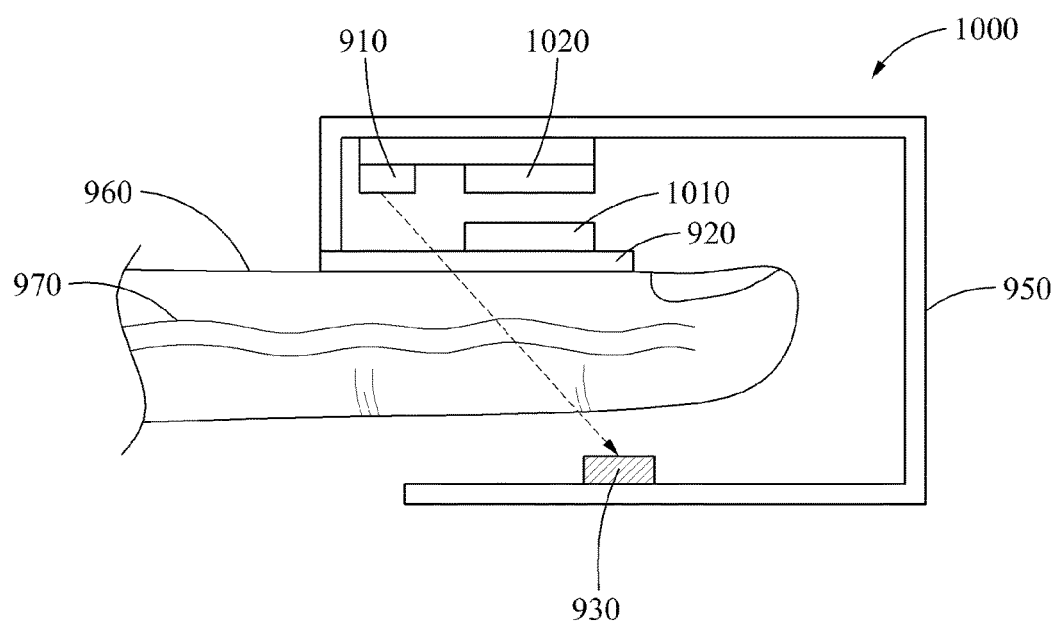

FIGS. 9 and 10 are diagrams illustrating additional examples of biosignal measuring sensors having a transmissive structure. Referring to FIG. 9, a biosignal measuring sensor 900 includes an optical source 910, an inserted layer 920, an optical detector 930, a displacement and force detector 940, and a shield 950. The optical source 910 emits a light towards a target 960, and the inserted layer 920 transmits the light emitted from the optical source 910. The optical detector 930 detects a light transmitted through the target 960. The displacement and force detector 940 is provided on the inserted layer 920 and detects a change in surface displacement or in contact force of the target 960 depending on a dilatation and a contraction of a blood vessel 970 in the target 960. For example, a piezoelectric element or a strain gauge may be used as the displacement and force detector 940, and the piezoelectric element or the strain gauge may be formed on the inserted layer 920. FIG. 10 illustrates a biosignal measuring sensor 1000 in a transmissive structure including a displacement and force detector configured to detect a change in surface displacement or contact force of the target 960 by measuring a change in capacitance based on a change in distance between a first electrode 1010 and a second electrode 1020.

Figure 11:
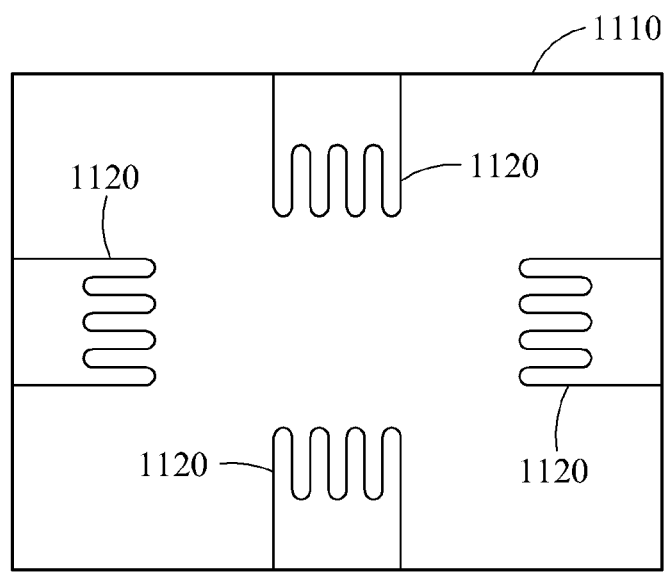
FIGS. 11 and 12 are diagrams illustrating structures of examples of inserted layers used to detect a surface displacement or a contact force of a target.
Figure 12:
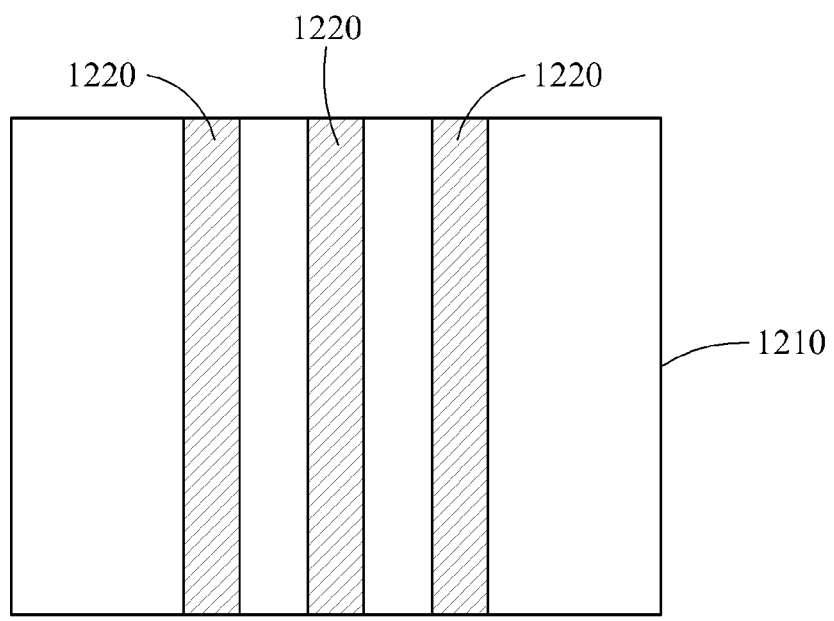

FIGS. 11 and 12 illustrates structures of examples of inserted layers used to detect a surface displacement or a contact force of a target. Referring to FIG. 11, a strain gauge 1120 is formed on an inserted layer 1110 to measure a strain occurring due to a deformation of the inserted layer 1110. A vibration of a pulse wave in a target may be exhibited as a vibration of a surface of the target, and the vibration of the surface of the target may apply a strain to the inserted layer 1110 attached to the surface of the target. The inserted layer 1110 may be deformed by the strain, and the strain gauge 1120 may detect, as an electrical signal, the strain applied to the inserted layer 1110.

Referring to FIG. 12, a first electrode 1220 is formed on an inserted layer 1210. The first electrode 1220 forms a capacitor along with a second electrode separate from the first electrode 1220, and a biosignal measuring sensor measures a change in capacitance based on a change in distance between the first electrode 1220 and the second electrode. For example, the first electrode 1220 may be formed by patterning a conductive material on the inserted layer 1210, or by doping an area of the inserted layer 1210 with impurities.

Figure 13:
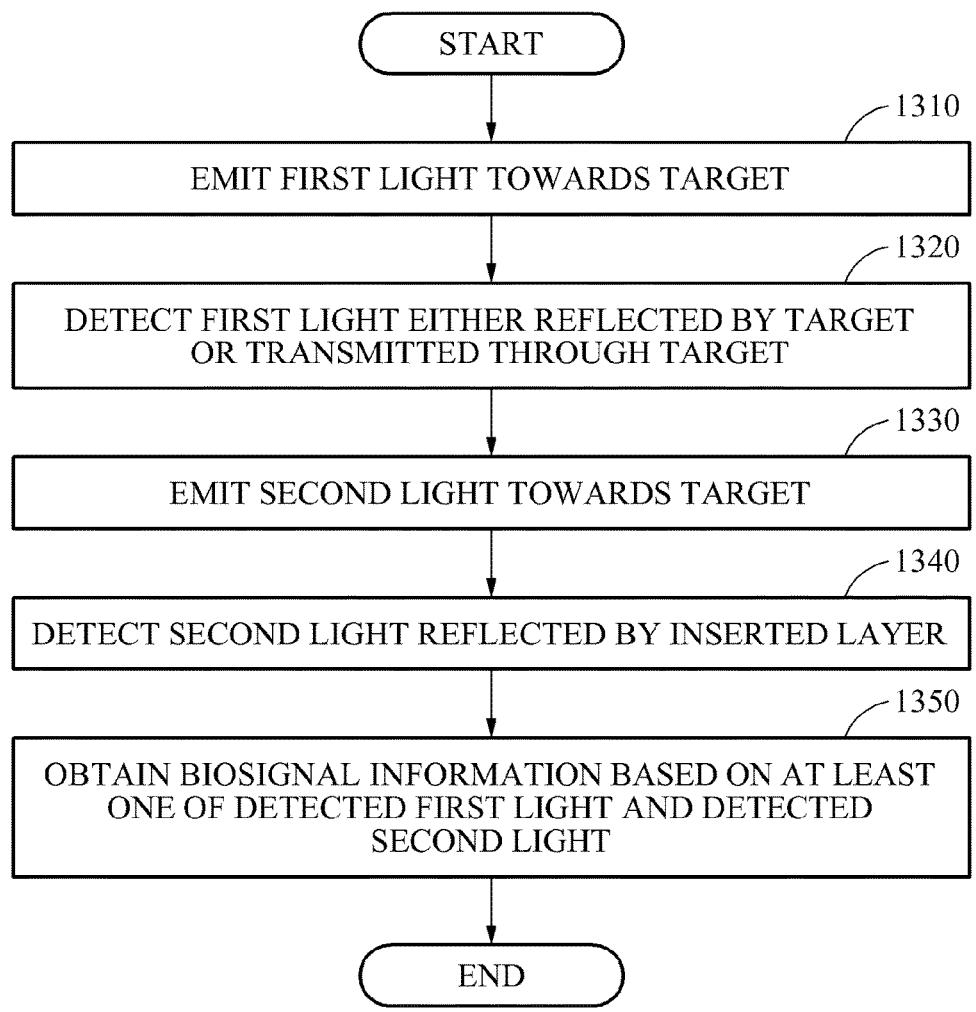
FIG. 13 is a flowchart illustrating an example of a method of measuring a biosignal.

FIG. 13 is a flowchart illustrating an example of a method of measuring a biosignal. The method of measuring a biosignal, hereinafter referred to as a biosignal measuring method, may be performed by a biosignal measuring apparatus described in the foregoing. The descriptions provided with reference with FIGS. 1 through 12 may be applied to a description to be provided with reference to FIG. 13.

Referring to FIG. 13, in operation 1310, the biosignal measuring apparatus emits a first light towards a target to be measured. The biosignal measuring apparatus may emit the first light that is, for example, infrared light or red visible light having a first wavelength. The emitted first light may reach the target after being transmitted through an inserted layer. In an example, the first light arrived at the target may be reflected from a deep portion of the target. In operation 1320, the biosignal measuring apparatus detects a first received light that corresponds to the first light that is reflected by the target after being transmitted through the inserted layer. In another example, in operation 1320, the biosignal measuring apparatus detects a first received light that corresponds to the first light that is transmitted through the target.

In operation 1330, the biosignal measuring apparatus emits a second light towards the target. The biosignal measuring apparatus may emit the second light having a relatively shorter wavelength than the first light, for example, blue visible light. The emitted second light may be reflected by the inserted layer. In operation 1340, the biosignal measuring apparatus detects a second light reflected by the inserted layer.

In operation 1350, the biosignal measuring apparatus obtains biosignal information based on at least one of the detected first light and the detected second light. The biosignal measuring apparatus extracts the biosignal information based on a signal associated with the detected first light and a signal associated with the detected second light, having a desired signal quality, or extracts the biosignal information by combining the two signals.

The apparatuses, units, modules, devices, and other components illustrated in FIGS. 1 through 4 that perform the operations described herein with respect to FIG. 13 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIG. 13. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for measuring a biosignal, comprising:
   an optical source configured to emit a first light and a second light towards a target;
   an inserted layer configured to transmit the first light and to reflect the second light; and
   an optical detector configured to detect a first received light that corresponds to the first light reflected by or transmitted through the target, and to detect a second received light that corresponds to the second light reflected by the inserted layer.

2. The apparatus of claim 1, wherein a wavelength of the first light is longer than a wavelength of the second light.

3. The apparatus of claim 1, wherein the first light is a light polarized at a first angle;
   the second light is a light polarized at a second angle different from the first angle; and
   the inserted layer is configured to transmit the light polarized at the first angle and reflect the light polarized at the second angle.

4. The apparatus of claim 1, wherein the first received light has an optical property that varies based on a change in blood flow in the target.

5. The apparatus of claim 1, wherein the second received light has an optical property that varies based on a change in surface displacement of the target or a change in contact force on a surface of the target.

6. The apparatus of claim 1, wherein the inserted layer is physically deformable by an external force.

7. The apparatus of claim 1, wherein the inserted layer is either a sticker or a tattoo attached to a surface of the target.

8. The apparatus of claim 1, further comprising:
a signal processor configured to extract biosignal information based on at least one signal input from the optical detector.

9. The apparatus of claim 1, wherein the apparatus for measuring a biosignal operates through being comprised in a mobile device or a wearable device.

10. The apparatus of claim 1, further comprising:
a shield configured to prevent an inflow of an external light into the optical detector.

11. The apparatus of claim 10, wherein the optical source comprises:
a first optical source disposed on one side of the shield and configured to emit the first light towards the target; and
a second optical source disposed on another side of the shield and configured to emit the second light towards the target.

12. The apparatus of claim 10, wherein the optical detector comprises:
a first optical detector disposed on one side of the shield and configured to detect the first light transmitted through the target; and
a second optical detector disposed on another side of the shield and configured to detect the second light reflected by the inserted layer.

13. The apparatus of claim 1, wherein the insertion layer is configured to transmit the first light and to reflect the second light based on a wavelength of a light incident on the insertion layer.

14. An apparatus for measuring a biosignal, comprising:
an optical source configured to emit a light towards a target;
an inserted layer configured to transmit the light;
an optical detector configured to detect a light reflected by the target or a light transmitted through the target; and
a displacement and force detector configured to detect either a change in displacement on a surface of the target or a change in contact force on the surface of the target.

15. The apparatus of claim 14, wherein the displacement and force detector is disposed in a single layer structure or a multilayer structure in the inserted layer.

16. The apparatus of claim 14, wherein the displacement and force detector is configured to detect either the change in displacement or the change in contact force by using a piezoelectric element or a piezoresistive element.

17. The apparatus of claim 14, wherein the displacement and force detector comprises:
a first electrode formed on the inserted layer; and
a second electrode located to be spaced apart from the first electrode.

18. The apparatus of claim 17, wherein the displacement and force detector is configured to detect at least one of the change in displacement and the change in contact force based on a change in capacitance based on a change in distance between the first electrode and the second electrode.

19. The apparatus of claim 14, further comprising:
a signal processor configured to obtain biosignal information of the target based on either a signal to be input from the optical detector or a signal to be input from the displacement and force detector.

20. A method of a biosignal measuring apparatus to measure a biosignal, the method comprising:
emitting a first light towards a target;
detecting a first received light corresponding to the first light either reflected by the target or transmitted through the target;
emitting a second light towards the target;
detecting a second received light corresponding to the second light that is reflected by an inserted layer; and
obtaining biosignal information of the target based on at least one of the detected first light and the detected second light,
wherein the inserted layer is configured to transmit the first light and to reflect the second light.

* * * * *